US00PP22858P3

(12) United States Plant Patent
Breach

(10) Patent No.: US PP22,858 P3
(45) Date of Patent: Jul. 17, 2012

(54) APPLE TREE NAMED 'NC1'

(50) Latin Name: ***Malus domestica* Borkh.**
Varietal Denomination: NC1

(76) Inventor: John Roland Breach, Staplehurst (GB)

( * ) Notice: Subject to any disclaimer, the term of this patent is extended or adjusted under 35 U.S.C. 154(b) by 0 days.

(21) Appl. No.: 12/932,901

(22) Filed: Mar. 8, 2011

(65) Prior Publication Data

US 2011/0225685 P1 Sep. 15, 2011

(30) Foreign Application Priority Data

Mar. 10, 2010 (EM) ..... 2010/0592

(51) Int. Cl.
*A01H 5/00* (2006.01)

(52) U.S. Cl. ..... Plt./161

(58) Field of Classification Search ..... Plt./161
See application file for complete search history.

*Primary Examiner* — Annette Para
(74) *Attorney, Agent, or Firm* — Michelle Bos

(57) ABSTRACT

A new apple tree (*Malus domestica* Borkh.) named 'NC1' is described. 'NC1' is the result of a cross between 'Cox's Orange Pippin' and 'Golden Delicious.' The fruit of 'NC1' is notable for its late maturity, attractive appearance and long shelf life as compared to its parents.

4 Drawing Sheets

Latin name: *Malus domestica* Borkh.
Variety denomination: 'NC1'.

PRIORITY

This application claims priority of European Community Plant Variety Rights application serial no. 2010/0592 filed Mar. 10, 2010.

BACKGROUND OF THE VARIETY

'NC1' is a new and distinct cultivar of apple tree (*Malus domestica* Borkh.). This new cultivar is a product of the open pollination of 'Cox's Orange Pippin' (not patented) in a commercial orchard near Staplehurst, Kent, United Kingdom in 1978. DNA analysis conducted in 2009 indicates that the male parent of 'NC1' is 'Golden Delicious' (not patented). The inventor noted the healthy appearance and superior eating quality of the fruit, and reserved its seeds for planting in 1979. This tree was grown to maturity and observed until 1998, when it was first asexually propagated by budding at Villers-Cotteret, France. The new variety has since been observed through successive asexually propagated generations, and has been found to retain the desireable characteristics of the originally discovered fruit.

BRIEF DESCRIPTION OF THE VARIETY

'NC1' was first selected for its healthy appearance and superior eating quality. It is distinguished from its parents 'Cox's Orange Pippin' and 'Golden Delicious' by the characteristics shown in Table 1 below.

TABLE 1

Comparison of 'NC1' to 'Cox's Orange Pippin' and 'Golden Delicious'

| | NC1 | Cox Orange Pippin | Golden Delicious |
|---|---|---|---|
| Tree shape | Upright | Upright | Open |
| Fruit size | Medium to Large | Medium | Medium to large |
| Harvest date (Loire Valley, France) | 20th of September | 28th of August | 15th of September |
| Skin coloration | Red Orange with a yellow-green background | Orange with a yellow background | Yellow with a cream green background |
| Storage ability | Medium to good | Weak | Medium to good |
| Shelf-life | Medium to good | Weak | Medium |
| Aroma | Intense to high acidity | Intense | Medium |
| Firmness | Medium to Firm | Soft to Medium | Medium |

BRIEF DESCRIPTION OF THE PHOTOGRAPHS

Figure 1:
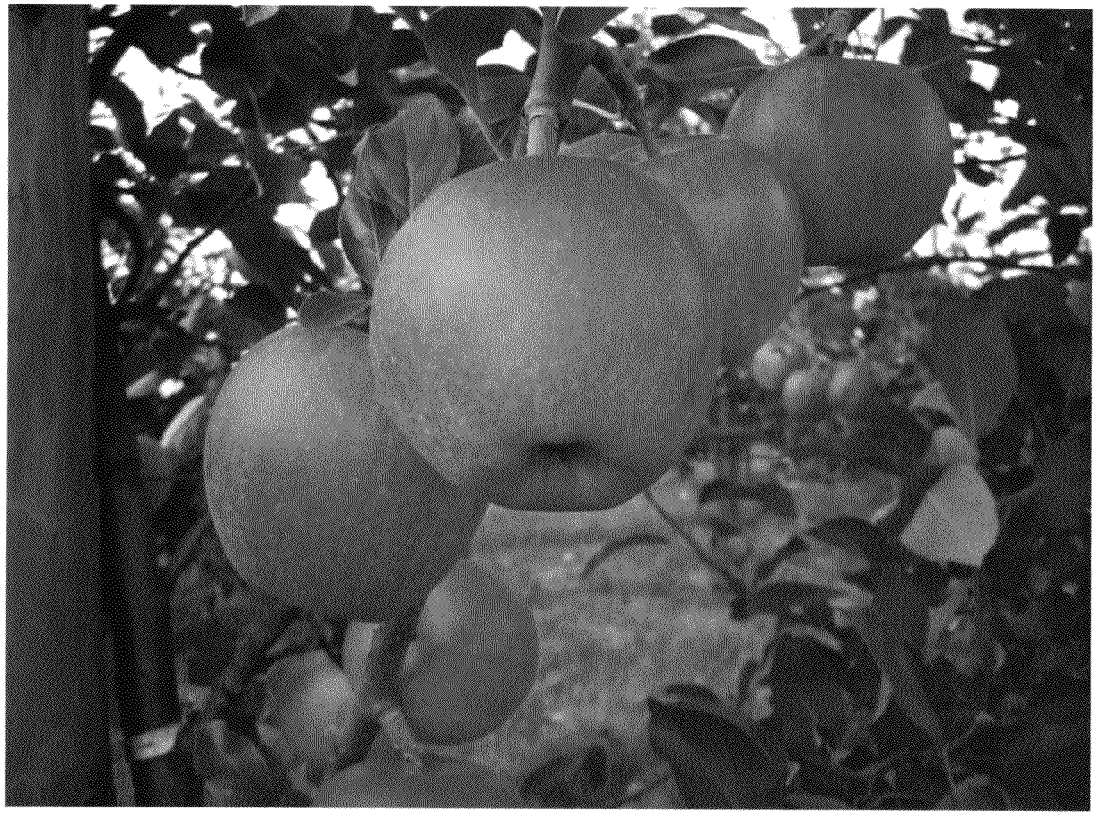
Figure 2:
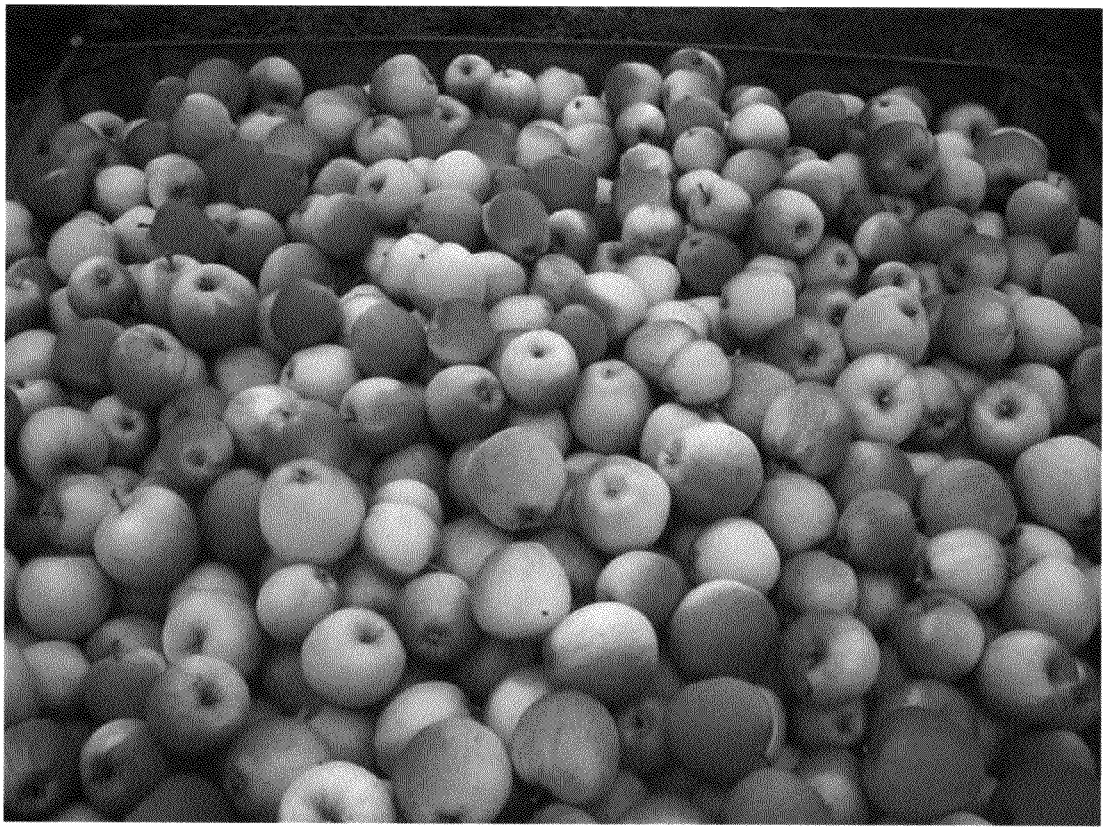
Figure 3:
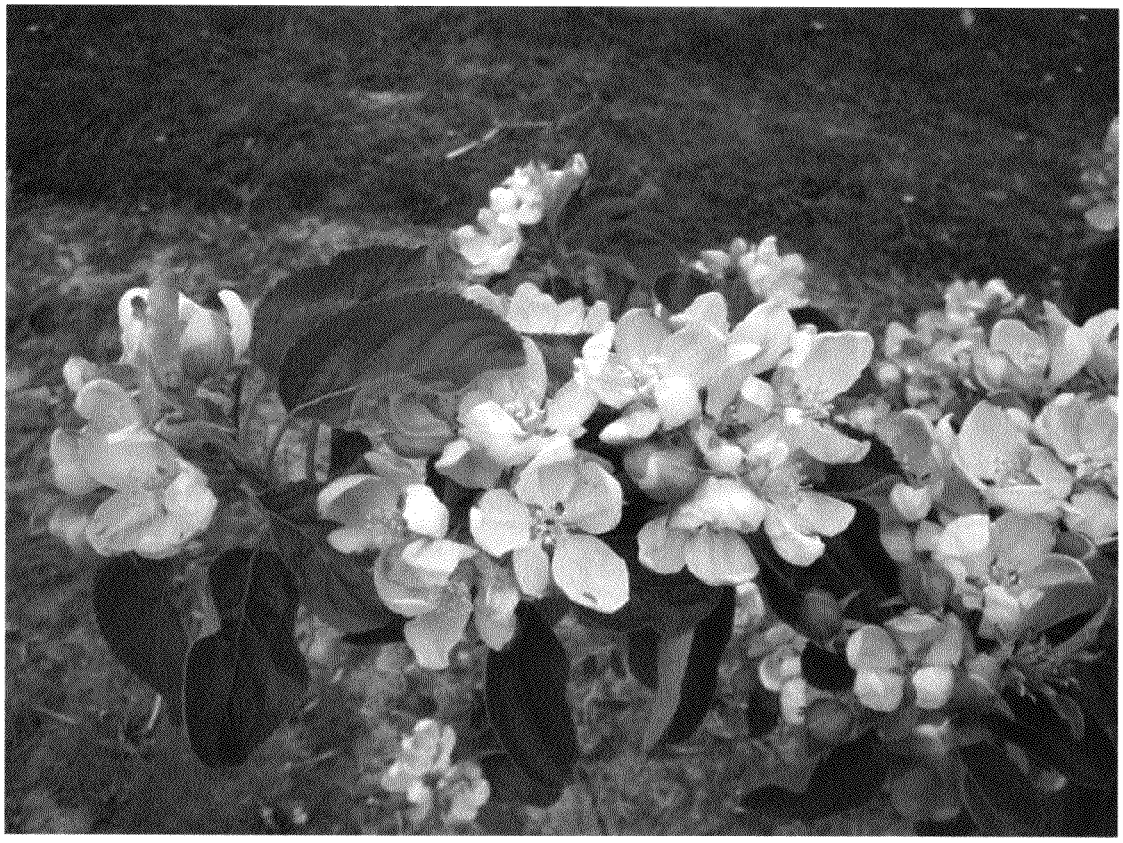
Figure 4:
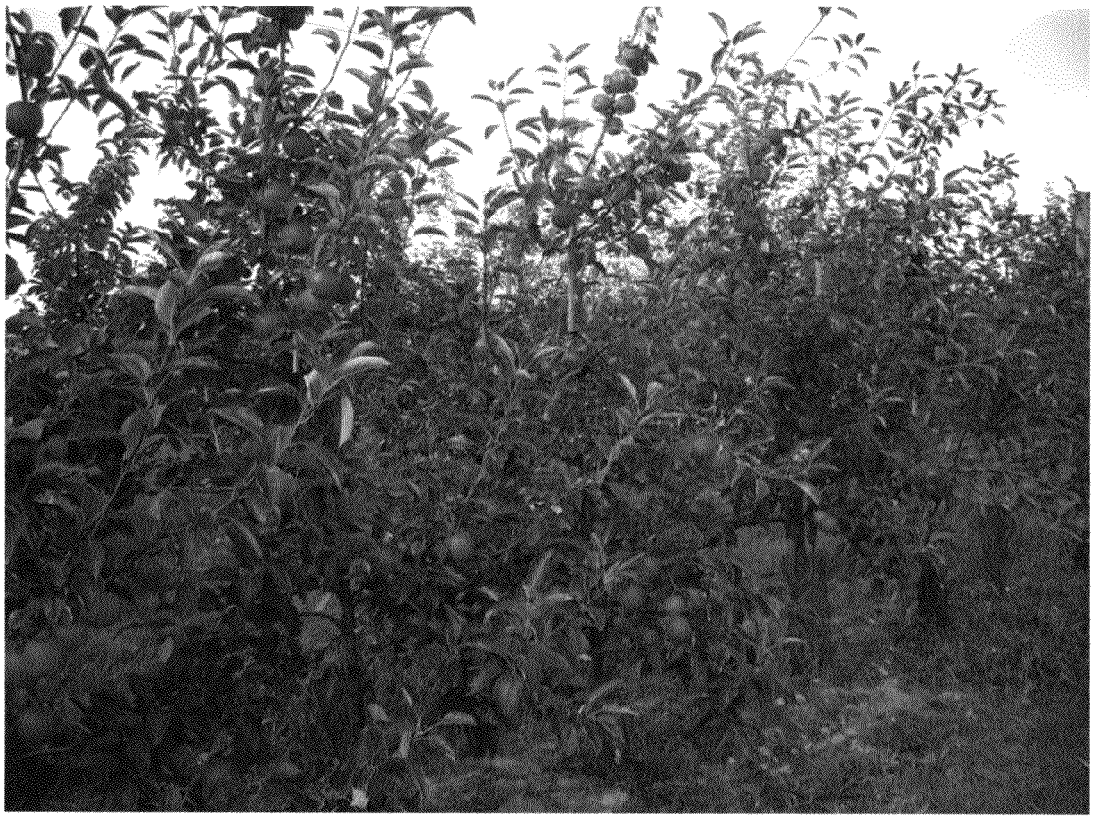

FIG. 1 shows fruit, branch, and leaves of 'NC1';
FIG. 2 shows fruit of 'NC1';
FIG. 3 shows leaves and blossoms of 'NC1'; and
FIG. 4 shows a tree of 'NC1'.

DETAILED BOTANICAL DESCRIPTION OF THE VARIETY

The following detailed botanical description is based on observations made near the Loire Valley, France, during the 2010 and 2011 growing seasons, of 'NC1' trees planted in 2007. The observed trees were grown on PAJAM®2 Cepiland rootstock. Photographs were taken during the 2010 growing season. All colors are described according to The Royal Horticultural Society Colour Chart. It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
*Vigor*.—Quite strong.
*Type*.—Ramified.
*Habit*.—Upright.
*Height*.—2.55 m.
*Trunk diameter* (*at* 30 *cm above the graft*).—5.2 cm.
*Bark texture*.—Smooth with large, prominent lenticels.
*Bark coloration*.—Grey-brown N200C.

Branch (fruiting branches located at around 1 m above the graft union):
*Length*.—1.3 m.
*Diameter*.—2.2 cm.
*Crotch angle*.—60°.
*Bark color*.—Reddish-brown N199C.
*Lenticel length*.—1 mm.
*Lenticel color*.—Grey-white N155A.
*Number of lenticels per cm*$^2$.—9.

One year old shoot:
*Length*.—12 cm.
*Color*.—Reddish-brown N199C.
*Pubescence*.—Medium.
*Thickness*.—0.44 cm.
*Internode length*.—4 cm.
*Pubescence*.—Medium.
*Number of lenticels per cm*$^2$.—3.5.

Flower buds:
*Quantity per spur*.—2 to 3.
*Shape*.—Conical.
*Length*.—Medium, 12 mm.
*Diameter*.—Medium, 8 mm.
*Color*.—Pink 63B.

Flowers:
*Diameter of fully open flower*.—48 mm.
*Relative position of petal margin*.—Free.
*Number per cluster*.—5 to 6.
*Date of first bloom*.—April 6.
*Date of full bloom*.—April 11, medium to late.
*Pollination requirement*.—Golden, Braeburn.

Petals:
*Quantity per flower*.—5.
*Shape*.—Ovate.
*Length*.—Long, 23 mm.
*Width*.—Wide, 17 mm.
*Apex*.—Round.
*Base*.—Pointed.
*Margin*.—Smooth.
*Coloration of upper surface*.—White with pink 64D.
*Coloration of lower surface*.—Pink 63D.

Pistils:
*Size*.—12 mm.
*Color*.—Yellow-green 145B.

Stigma:
*Size*.—1 mm.
*Color*.—Light yellow 8C.

Style:
*Size*.—9 mm.
*Color*.—Yellow-green 145B.

Ovary:
*Size*.—3.5 mm.
*Color*.—Light green 138D.

Anthers:
*Quantity*.—Numerous, average 18.
*Size*.—2 mm.
*Presence of pollen*.—Yes.
*Color of pollen*.—Light yellow 8C.

Pedicel:
*Length*.—19 mm.
*Diameter*.—Thin, 1.2 mm.
*Color*.—Light green 138D.

Sepals:
*Quantity*.—5.
*Coloration*.—Light green 138D.
*Shape*.—Conical pointed.
*Margin*.—Smooth.

Leaves:
*Shape*.—Oblanceolate.
*Length*.—94 mm.
*Width*.—41 mm.
*Length/width ratio*.—2.3.
*Blade margin*.—Crenate.
*Apex*.—Acuminate.
*Base*.—Oblique.
*Color of upper surface*.—Green 137C.
*Color of lower surface*.—Green 146C.
*Attitude in relation to shoot*.—Upward.

Petiole:
*Length*.—32 mm.
*Diameter*.—1.7 mm.
*Coloration*.—Green 137C.

Fruit:
*Quantity per cluster*.—5 (before thinning).
*Diameter*.—74 mm.
*Weight*.—190 g.
*Ratio of height to width*.—0.8.
*General shape in profile*.—Conical.
*Position of maximum diameter*.—In the middle.
*Ribbing*.—Absent to weak.
*Crowning at calyx end*.—Moderate.
*Size of eye*.—Medium.
*Aperture of eye*.—Closed.
*Length of sepal*.—Medium (5 mm).
*Bloom of skin*.—Absent to weak.
*Greasiness of skin*.—Moderate.
*Background color of skin*.—Yellow 2C.
*Amount of over color*.—Medium (40% to 60%).
*Over color of skin*.—Red 45A.
*Intensity of over color*.—Medium.
*Pattern of over color*.—Blush with well-defined stripes.
*Amount of russet around stalk cavity*.—Medium.
*Amount of russet on cheeks*.—Slight.
*Area of russet around eye basin*.—Very slight.
*Length of stalk*.—2 cm.
*Thickness of stalk*.—3 to 4 mm.
*Depth of stalk cavity*.—Medium.
*Width of stalk cavity*.—Medium.
*Depth of eye basin*.—Deep.
*Width of eye basin*.—Narrow.
*Firmness of flesh*.—9 kg at harvest.
*Flesh texture*.—Medium to coarse.
*Aroma*.—Highly aromatic with high acid and good sugar.
*Juiciness*.—Medium.
*Brix*.—14° Brix.
*Flesh coloration*.—Light yellow 4D.
*Stem coloration*.—Brown 199A.

Seeds:

*Quantity per fruit*.—6.

*Shape*.—Long conical.

*Coloration*.—Dark brown 200B.

Harvest:

*Time for harvest*.—September 20 (4 to 5 days after Golden Delicious).

*Number of picks*.—2.

*Amount of fruit produced per tree per harvest*.—13 kg.

Disease resistance/susceptibility: Some tolerance to European Canker (*Nectria galligena*); medium susceptibility to scab and mildew.

Market use: Fresh market, dessert quality apple.

I claim:

1. A new and distinct apple tree substantially as described and illustrated herein.

* * * * *